United States Patent
Takasaki et al.

(10) Patent No.: US 11,279,344 B2
(45) Date of Patent: Mar. 22, 2022

(54) PREEMPTIVE MITIGATION OF COLLISION RISK

(71) Applicant: INTERNATIONAL BUSINESS MACHINES CORPORATION, Armonk, NY (US)

(72) Inventors: Kenichi Takasaki, Shibuya (JP); Mari A. Fukuda, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 425 days.

(21) Appl. No.: 16/205,718

(22) Filed: Nov. 30, 2018

(65) Prior Publication Data
US 2020/0172091 A1    Jun. 4, 2020

(51) Int. Cl.
*B60W 30/09* (2012.01)
*B60W 30/095* (2012.01)
(Continued)

(52) U.S. Cl.
CPC ............... *B60W 30/09* (2013.01); *A61B 5/18* (2013.01); *A61B 5/291* (2021.01); *A61B 5/316* (2021.01);
(Continued)

(58) Field of Classification Search
CPC ............. B60W 30/09; B60W 30/0953; B60W 50/0097; B60W 50/14; B60W 2540/22;
(Continued)

(56) References Cited

U.S. PATENT DOCUMENTS

| 6,223,125 B1* | 4/2001 | Hall | G08G 1/164 |
| | | | 701/301 |
| 9,751,534 B2* | 9/2017 | Fung | G16H 50/20 |

(Continued)

FOREIGN PATENT DOCUMENTS

| JP | 2015035081 A | 2/2015 |
| JP | 2017061192 A | 3/2017 |

OTHER PUBLICATIONS

Disclosed Anonymously, "Delivers more excitement and driving pleasure by detecting, analyzing and responding to driver's brainwaves in real time", Nissan Motor Company Global Website, [retrieved on Jul. 24, 2018], 2 pages, Retrieved from the Internet: <https://www.nissan-global.com/JP/TECHNOLOGY/OVERVIEW/b2v.html>.

(Continued)

*Primary Examiner* — Redhwan K Mawari
(74) *Attorney, Agent, or Firm* — Anthony M. Pallone

(57) ABSTRACT

A method, computer system, and a computer program product for preemptive collision mitigation is provided. The present invention may include calculating a future position of a first vehicle based on carprobe data from a first vehicle, wherein the carprobe data contains neural data of an operator of the first vehicle. The present invention may also include calculating a distance between the future position of the first vehicle and a future position of a second vehicle. The present invention may then include determining the calculated distance between the future position of the first vehicle and the future position of the second vehicle is below a threshold distance.

24 Claims, 8 Drawing Sheets

(51) Int. Cl.
    B60W 50/00    (2006.01)
    A61B 5/18     (2006.01)
    A61B 5/00     (2006.01)
    B60W 50/14    (2020.01)
    A61B 5/291    (2021.01)
    A61B 5/316    (2021.01)
(52) U.S. Cl.
    CPC ............ *A61B 5/6893* (2013.01); *A61B 5/746* (2013.01); *B60W 30/0953* (2013.01); *B60W 50/0097* (2013.01); *B60W 50/14* (2013.01); *B60W 2540/22* (2013.01); *B60W 2710/18* (2013.01); *B60W 2720/106* (2013.01)
(58) Field of Classification Search
    CPC ........ B60W 2710/18; B60W 2720/106; A61B 5/291; A61B 5/316; A61B 5/18; A61B 5/6893; A61B 5/746
    See application file for complete search history.

(56)                References Cited

U.S. PATENT DOCUMENTS

| 2009/0040054 | A1  | 2/2009  | Wang et al.      |              |
|--------------|-----|---------|------------------|--------------|
| 2016/0101785 | A1  | 4/2016  | Takahashi et al. |              |
| 2016/0318445 | A1  | 11/2016 | Sugimoto         |              |
| 2016/0357262 | A1* | 12/2016 | Ansari           | G06Q 10/0833 |
| 2016/0364678 | A1* | 12/2016 | Cao              | G06Q 50/30   |
| 2017/0178498 | A1* | 6/2017  | Mcerlean         | G08G 1/166   |
| 2017/0269599 | A1* | 9/2017  | Ansari           | G05D 1/0212  |
| 2017/0305349 | A1  | 10/2017 | Naboulsi         |              |
| 2018/0268695 | A1* | 9/2018  | Agnew            | B60K 28/066  |
| 2019/0016338 | A1* | 1/2019  | Ishioka          | B60W 30/18163|
| 2019/0088136 | A1* | 3/2019  | Nagata           | G08G 1/166   |
| 2019/0168732 | A1* | 6/2019  | Tashiro          | B60W 10/10   |
| 2019/0187700 | A1* | 6/2019  | Zheng            | G06F 9/4887  |
| 2019/0283741 | A1* | 9/2019  | Toda             | B60W 10/184  |
| 2019/0325325 | A1* | 10/2019 | Monteil          | G08G 1/096844|
| 2019/0329738 | A1* | 10/2019 | Wilson           | B60S 3/002   |
| 2020/0152340 | A1* | 5/2020  | Anvari           | H04L 67/12   |
| 2020/0172091 | A1* | 6/2020  | Takasaki         | A61B 5/316   |
| 2020/0334125 | A1* | 10/2020 | Degaonkar        | H04L 43/0817 |

OTHER PUBLICATIONS

Haufe et al., "EEG potentials predict upcoming emergency brakings during simulated driving", Journal of Neural Engineering, Jul. 28, 2011, 11 pages, vol. 8, IOP Publishing.

Lew, et al., "Single trial prediction of self-paced reaching directions from EEG signals", Frontiers in Neuroscience, Aug. 2014, 13 pages, vol. 8, Article 222.

Mell et al., "The NIST Definition of Cloud Computing", National Institute of Standards and Technology, Special Publication 800-145, Sep. 2011, pp. 1-7.

* cited by examiner

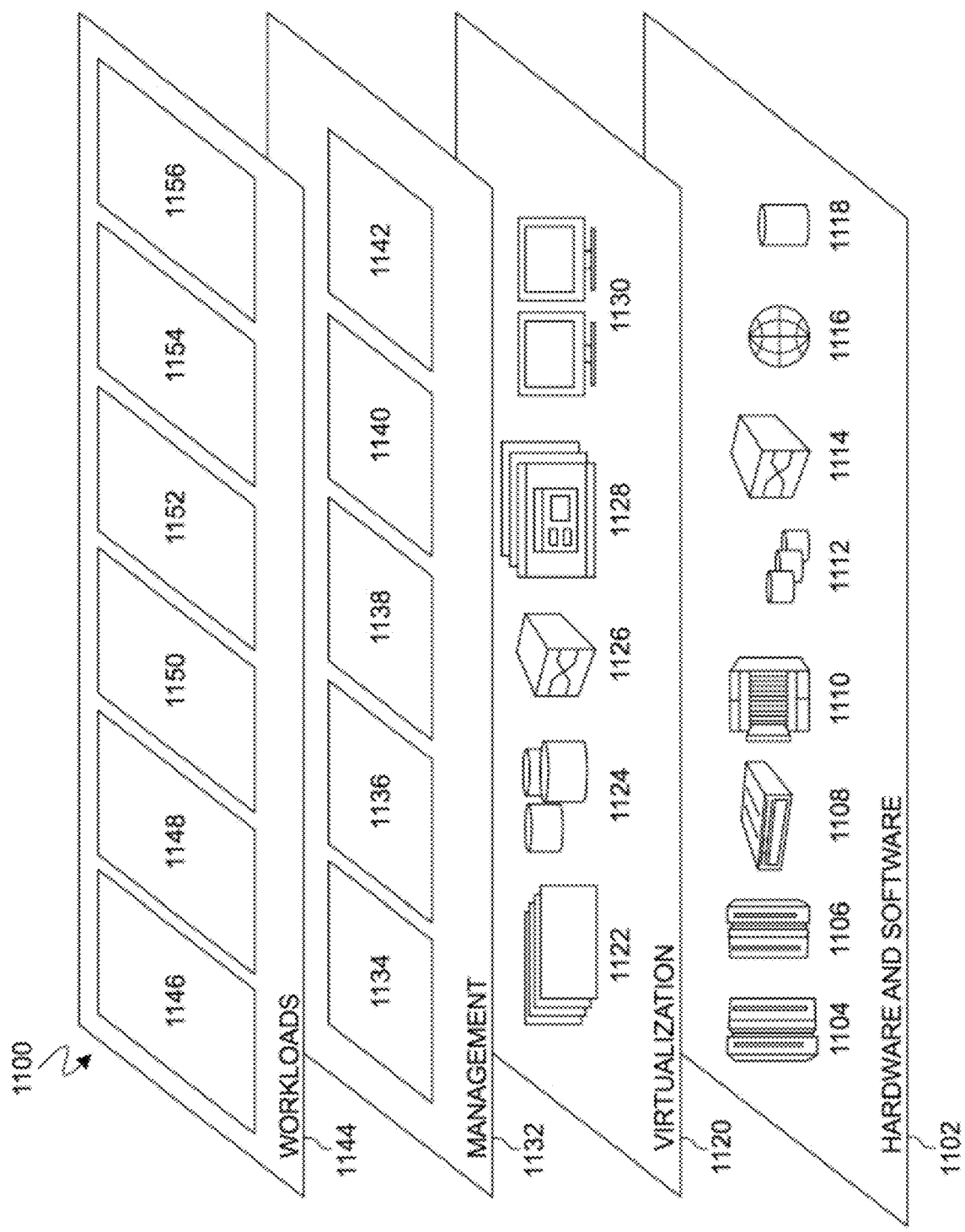

PREEMPTIVE MITIGATION OF COLLISION RISK

BACKGROUND

The present invention relates generally to the field of computing, and more particularly, collision risk mitigation. A collision event, such as a motor vehicle collision, may include an occurrence in a location when one or more motor vehicles makes an impact with each other or with an object on the road. A collision event may result in damages, both injury to a person and property damages.

The motor vehicle may be controlled by a driver and human factors may be associated with the driver, such as biological factors. Detecting human biological factors may assist in mitigating unsafe driving conditions. Collisions may be caused by factors, such as a sudden movement by a driver, an interruption made by another vehicle, an interruption made by a pedestrian or an animal, or a driver entering an incorrect direction on a roadway. Known art may determine the level of dangerous driving in real-time based on biological data of a driver and image data.

Current technology may also relate to automotive danger such that a collision may notify nearby drivers of the unsafe driving activity, such as when a driver causes an accident or when a driver travels in the incorrect direction on a road in an automobile. Although nearby drivers may be notified for safety purposes, the notification is made after the occurrence of the unsafe driving activity. Notifying nearby drivers after a collision has taken place may not secure the safety of nearby drivers and pedestrians.

Conventional technology also may use data such as maps, events and vehicle travel to be limited by a single vehicle. Limiting the data to a single vehicle may not allow for a determination of safety based on a single driver without additional data of the surroundings. Conventional art may also have the ability to measure the state of a driver (e.g., tired) in real-time, however, may not have the ability to detect risk in advance or before an incident occurs.

SUMMARY

Embodiments of the present invention disclose a method, computer system, and a computer program product for preemptive collision mitigation. The present invention may include calculating a future position of a first vehicle based on carprobe data from a first vehicle, wherein the carprobe data contains neural data of an operator of the first vehicle. The present invention may also include calculating a distance between the future position of the first vehicle and a future position of a second vehicle. The present invention may then include determining the calculated distance between the future position of the first vehicle and the future position of the second vehicle is below a threshold distance.

An advantage may allow a driver from an originating vehicle and a driver from a nearby vehicle to avoid a collision by receiving an alert prior to the fruition of an unsafe driving event. Collision mitigation may be based on neural data received in carprobe data. Another advantage may include, for example, a forced stop to the driving operation of the originating vehicle to avoid a collision.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 7 is a block diagram of functional layers of the illustrative cloud computing environment of FIG. 6, in accordance with an embodiment of the present disclosure.

DETAILED DESCRIPTION

Figure 1:
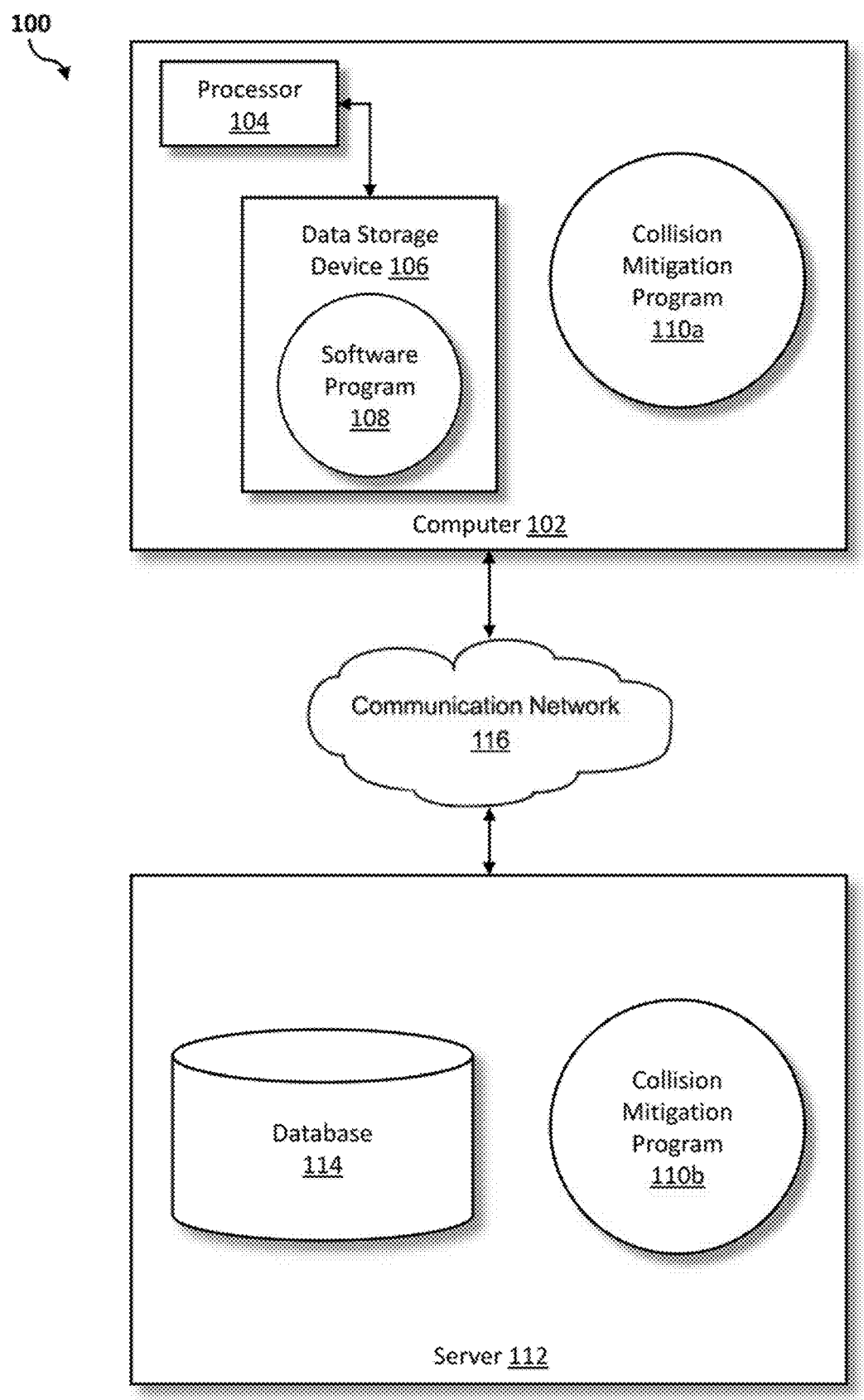
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The following described exemplary embodiments provide a system, method and program product for collision risk mitigation. As such, the present embodiment improves the field of collision risk mitigation by securing the safety of vehicles and pedestrians from sudden dangerous (i.e., unsafe) driving activities. More specifically, the present invention detects predicted motions of the driver based on the electroencephalograms (EEGs) of the driver before the driver commits the unsafe driving activity and then notifies nearby drivers and pedestrians of the anticipated activity.

As previously described, the present invention relates generally to the field of computing, and more particularly, collision risk mitigation. A collision event, such as a motor vehicle collision, may include an occurrence in a location when one or more motor vehicles makes an impact with each other or with an object on the road. A collision event may result in damages, both injury to a person and property damages. The motor vehicle may be controlled by a driver and various human factors may be associated with the driver, such as biological factors. Human biological factors may assist in mitigating collision.

Human biological factors, such as heartbeat and respiration rate may not provide a possible basis to enable a prediction of human motions prior to the actual human motion. Image analysis using a camera may also not provide a human motion prediction ahead of time. Therefore, it may be advantageous to, among other things, have the ability to predict human motions before the actual human motion is implemented.

According to at least one embodiment, predicting or anticipating motions of a driver before the motions are performed may allow preemptive notification to nearby drivers and pedestrians prior to the occurrence of an incident. Prior notification may provide sufficient notice to both an individual driver and to nearby individuals to avoid a collision or to mitigate damages of an unsafe driving condition.

Predicting human motion prior to the motion being performed by a human may be identified by using an electroencephalogram (EEG). An EEG may detect brain activity (i.e., brain activity data) by measuring the electrical activity of the brain. Measuring electrical activity may be accomplished by using, for example, electrodes attached to the scalp of an individual. The electrodes may detect brain waves and an EEG machine may amplify the brain wave signals. An EEG signal is safe and non-invasive to measure. A non-invasive EEG may detect brain activity using a brain-computer interface (BCI) that may measure electroencephalogram signals (i.e., EEG signals). One measurement may include movement-related cortical potentials that may represent EEG activity of an individual before and after a voluntary movement.

EEG research has evolved to enable ahead-of-time prediction of human motions that were not possible using biological factors. Known methods may use an EEG machine (e.g., an EEG headset or an EEG wireless headset) or EEG signals to detect driver preferences or discomforts to allow for the driving configuration in an autonomous driving mode to create, for example, driver assist movements that allow a better reaction time for drivers. Autonomous driving modes may also create a safe pattern that may align with driver expectations.

In addition to the neurological human elements being measured and analyzed, Internet of Things (IoT) technology may also be incorporated due to the multiple types of data that may be transmitted between various devices. IoT may include devices embedded with software, sensors, data storage, central processing units and the ability to connect to a network. An example of IoT may include devices for homes, buildings, vehicles, mobile devices, energy transmission, medical devices, infrastructure and other consumer applications. IoT devices may even communicate with backend infrastructures over a communication network. The various data that may be transferred may include structured data, unstructured data, master data, transactional data, event data or temporal data. Data may, for example, be stored on a server database or on multiple server databases. Data may be transferred across a communication network between devices such as a server, a sensor, an internet of things (IoT) device, a camera, a microphone, a personal computer, a smart phone, a tablet or a smart watch.

In the present embodiment, predicting human motions may be determined while the individual is operating a moving object or a mobile object. A moving object may include, for example, a wheelchair, a skateboard, a bike, a scooter, a motorcycle, a hoverboard, a recreation vehicle, a boat, a segway board, a vehicle or an automobile. A mobile object may, for example, be a device such as a smart phone used by a in individual operating a moving object. A mobile object may also be held by a pedestrian. A mobile object may, for example, be a smart phone, a smart watch or a tablet that is capable of transmitting data over a communication network.

Components of a moving object may include a device mounted on the moving object or a mobile object located on or in a moving object. For example, a vehicle mounted device may be a device mounted on an automobile or a smartphone mounted inside an automobile, both having the capabilities to receive and transmit data over a communication network. A vehicle mounted device may include a map service, an operation detector (e.g., a brain wave analysis component) and a real-time virtual vehicle cache (i.e., an agent). A vehicle mounted device may also include a telematics communication unit (TCU), a car navigation system or a smartphone. Each unit, device or system in the vehicle may have the capability of operating the map service, the operation detector and the real-time virtual vehicle cache.

In the present embodiment, data that may be analyzed as input data into a collision mitigation program may include brain activity data, map data and carprobe data. Brain activity data may be obtained from an EEG. For example, and individual wearing an EEG headset that may transmit data over a communication network. Map data may include a geolocation or global position method such as a global positioning system (GPS). The map data may also include a map matching service that matches raw GPS location coordinates from a vehicle device to the coordinates of the actual mapped road (i.e., link) network. Additionally, map data may include a link identification (i.e., a link ID). The link ID may include a unique ID assigned to the road and may be divided into specific sections in each map version.

An event server (e.g., a dynamic map manager) may also be used to provide geospatial functions and map-based analytics such as map matching, route search and real-time traffic event updates. A gateway (e.g., a vehicle data hub) may receive and process data from IoT devices or sensors, for example, by configuring the gateway to IBM® IoT Connected Vehicle Insights (IBM and all IBM-based trademarks and logos are trademarks or registered trademarks of International Business Machines Corporation and/or its affiliates). The gateway may include a transmitting section and a receiving section. A gateway may be used as a carprobe data gateway that may dispatch carprobe data sent by each vehicle to a different service, such as a map service (e.g., a map matching service) or a batch analysis (e.g., a driving behavior analysis).

A gateway (i.e., gateway device) may transfer information, for example, between servers and moving objects in a particular geographic region. The event server may manage events in a particular geographic region and may manage agents (i.e., environment agent or event agent). Agents may be assigned to various events that may handle different rules, for example, one environment agent may manage an image event of a driver turning the wrong way on a road by assessing a sign by using a camera. One other environment agent may manage, for example, the speed limit by assessing the speed a vehicle is traveling via a sensor. An environment agent may be assigned to the same region as an event server. Many event servers and environment agents may be used in one or more geographic regions. The gateway may also reallocate environment agents assigned to event servers to balance processing loads in the network system.

Carprobe data (i.e., a carprobe) may also be referred to, for example, as probe vehicle data (PVD) in the automotive industry or an intelligent transportation system (ITS). Carprobe data may collect real-time data relating to traveling locations and timing from sensors or IoT devices. Carprobe data may include, for example, geographic location, health status, driver data and events of interest.

Carprobe data may be transmitted to and processed by the gateway component. The processed carprobe data may then be transmitted to IoT components. For example, the gateway processed carprobe data is transferred to IBM® IoT Connected Vehicle Insights system components. The IBM® IoT Connected Vehicles Insights system may support carprobe data from a vehicle sensor, for example, as defined by ISO standard 22837.

Based on the received inputs, the collision mitigation program may add a link ID to carprobe data by performing map matching, for example, using a dynamic map manager. Adding a link ID to carprobe data may include EEG data that may indicate a predicted human operation. An analysis based on link ID data and EEG data added to carprobe data may provide an estimated future position, for example, carprobe data being sent every 1 second. If an estimated future position may result in an unsafe condition, the collision mitigation program may provide a driving assisted operation, such as a notification or an alert to an individual or a forced operation to a vehicle.

An operation detector may analyze carprobe data to determine if the carprobe data contains brain activity data. The operation detector may also calculate future positions based on the input data (e.g., carprobe, brain activity data and current position of a vehicle) and then obtain an position on a map that corresponds to the future position of the vehicle. The operation detector may be part of a vehicle device and may also have the ability to communicate or transmit data to a server via the gateway.

One use case that may be described herein is when a driver of a vehicle is about to make an unintentional or an intentional sudden move that may cause an interruption or danger while driving or operating the vehicle. The interruption may, for example, be veering out of the designated lane, making a sudden lane change or making a sudden turn around a corner or onto a different roadway. The sudden interruption while driving may be determined by measuring and analyzing the EEG of the driver who may have not yet performed the sudden interruption. The EEG analysis may detect and predict that the operation may be performed by the driver in the future. Information of the detected operation may be communicated, for example, by an IoT for automotive device to the drivers and the vehicles traveling in the vicinity of the originating vehicle driver to notify the other drivers to preemptively avoid the unsafe movement.

An alternate embodiment may include when a driver is about to intentionally or unintentionally make a wrong driving operation, such as driving the wrong way down a one-way street or driving towards a stationary object. The operation may be determined as being an unsafe driving operation based on map information maintained by, for example, IoT devices for automotive features. The unsafe driving activity may be communicated to nearby drivers or pedestrians to avoid an incident.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a collision mitigation program 110a. The networked computer environment 100 may also include a server 112 that is enabled to run a collision mitigation program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the collision mitigation program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the collision mitigation program 110a, 110b (respectively) to mitigate the risk of a collision. The collision mitigation method is explained in more detail below with respect to FIGS. 2, 3, 4A and 4B.

Figure 2:
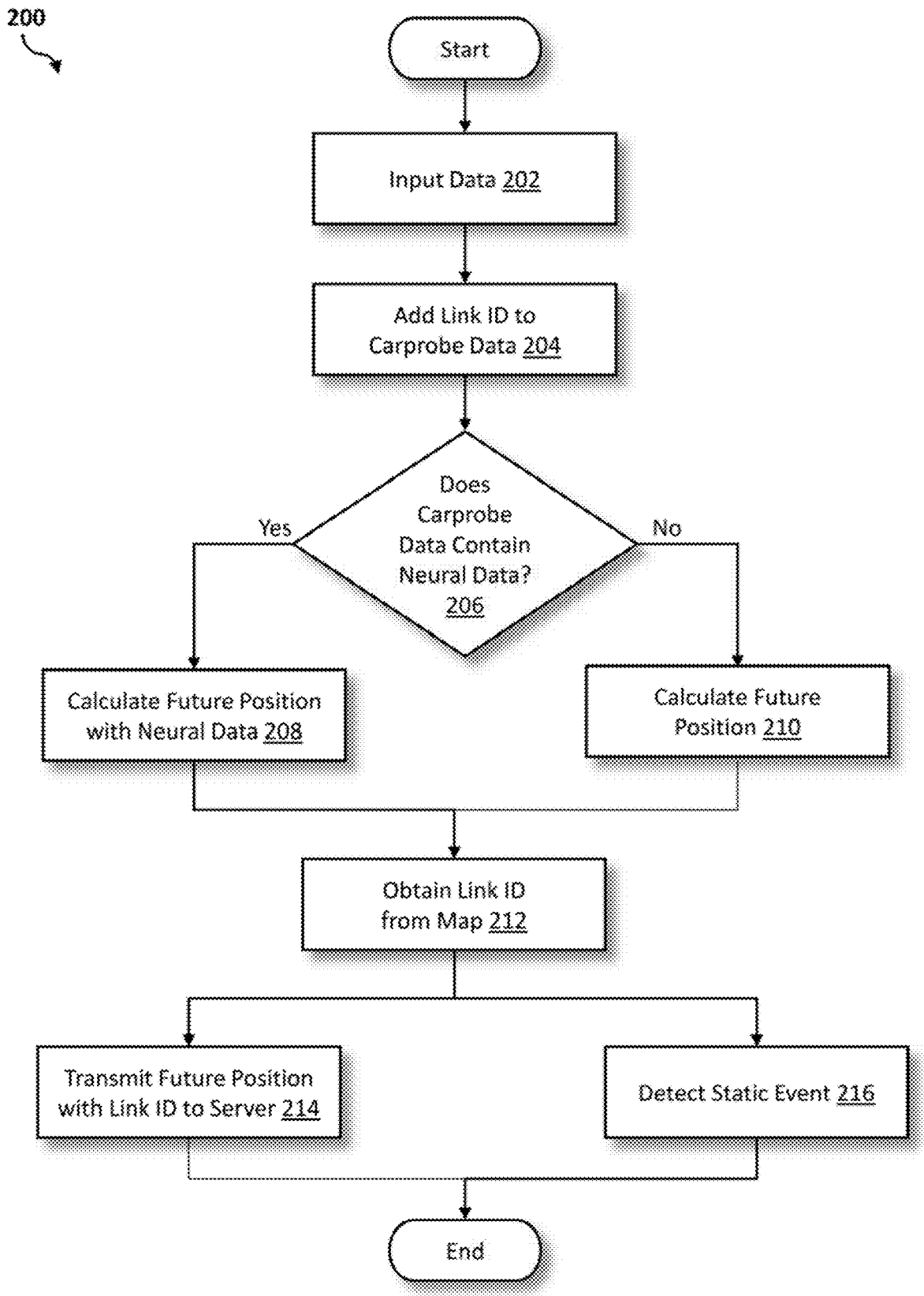
FIG. 2 is an operational flowchart illustrating an event process for a cache update and collision detection on a vehicle-mounted device.

Referring now to FIG. 2, an operational flowchart illustrating the exemplary event for a cache update and collision detection on a vehicle-mounted device process 200 used by the collision mitigation program 110a, 110b according to at least one embodiment is depicted.

At 202, data is received. Carprobe data, brain activity data and map data may be received by one or more devices in a communication network. The devices may be installed on a vehicle, placed in the vehicle or mounted in the vehicle. A device may include, for example, a vehicle mounted device, a smartphone or a gateway, an EEG headset or a combination of devices. Carprobe data (i.e., the carprobe) may include real-time data of travel location and timing obtained from IoT devices and sensors. Carprobe data may also include driver data such as events of interest, health status a behavior.

Brain activity data may be measured by an EEG headset and the EEG measurement may be transmitted via a communication network 116 to the vehicle device. Map data may include GPS data or a link ID. The link ID may be a unique ID assigned to the road (i.e., link) and divided into specific sections in each map version. For example, carprobe data from vehicle ID 1 (VID1) and brain activity data may include the following parameters.

| Carprobe Data | Brain Activity Data |
|---|---|
| Longitude = 139.01 | Right = True |
| Latitude = 35.45 | Left = False |
| Speed = 50 km/h | Acceleration = False |
| LinkID = 1 | Break = False |

At 204, a link ID is added to the carprobe data. Map matching may include the process of combining the link ID to carprobe data. Map matching may be performed, for example, in a vehicle by using pre-installed map data on the vehicle device to transmit a link ID to a carprobe. A result of map matching may provide a map matched link ID. An event server may be used in analyzing map matching, real-time traffic events or a route search to provide geospatial functions. A map matching service may match raw GPS location coordinates from the vehicle device to the coordinates of an actual mapped road network.

EEG data may be analyzed and measured, for example, using a BCI and the measurement may include movement-related cortical potentials that may predict human movement before the movement is made. Data indicative of the predicted operations of an individual may be sent to the carprobe data, such as steering to the left or right, accelerating and breaking.

An alternate embodiment may include a gateway handler that may be implemented, upon receiving carprobe data that includes brain activity data, to pass the carprobe data directly to an agent (i.e. a real-time virtual cache) without subjecting the carprobe data to a map matching process by a dynamic map manager or an event server.

At 206, the collision mitigation program 110a, 110b determines if the carprobe data contains neural data (i.e., brain activity data). The map matching data and the brain activity data may be added to the carprobe data at 204 based on the received data at 202. The received data at 202 may or may not contain neural data. Neural data may be received if the vehicle operation features calculated from an EEG measurement was above a predetermined threshold, then the vehicle may send the carprobe data with the brain activity data.

Previous driving behavior analysis may be stored on a database (e.g., database 114) and may be accessed to determine the level of brain activity that is measured. For example, if a user (i.e., a driver) typically keeps a large distance between the user vehicle and a vehicle in front of the user vehicle, then as that distance is reduced past a normal threshold for the user, the EEG may provide a higher brain activity data measurement.

Brain activity data may be measured when a user performs vehicle operations, such as breaking, accelerating and steering a vehicle. The collision mitigation program 110a, 110b may compare normal user EEG measurements using stored data with current user EEG measurements and if the difference in motor cortex (i.e., brain activity data) is over a threshold amount, then neural data may be added to the carprobe data.

Alternatively, for example, if the user of the EEG headset is operating the vehicle in a predicted manner and predicted to be operating the vehicle in a normal, controlled and predicted manner, the EEG measurement may not be added to the carprobe data.

If the collision mitigation program 110a, 110b determines that the carprobe data contains neural data at 206, then the future position is calculated with the neural data at 208. A future position may be estimated on the basis of the data indicative of a position, such as current direction, current speed and current acceleration and the predicted operation is included in the carprobe data with neural data (i.e., brain activity data). The future position may be estimated at various time frames in the future, for example, the future position is calculated at 1 second into the future and the carprobe data may be cached or transmitted every 1 second.

For example, if a vehicle is driving at a current speed and no acceleration is present for 1 second between one carprobe and the next carprobe, a future position may be calculated as follows:

$$y_1 = y_0 + \frac{1}{2}(v_0 + v_1)t,$$

$$v_1 = v_0 + a_0 t$$

where $y_1$, $v_1$, $y_0$, $v_0$, $a_0$ and t are future positions (i.e., distance), future speeds, current position (i.e., distance), current speed, current acceleration and time. The algorithm to calculate a future position may change according to a given situation or environment.

If the collision mitigation program 110a, 110b determines that the carprobe data does not contain neural data at 206, then the future position is calculated at 210. A future position may be estimated on the basis of the data indicative of a position, such as current direction, current speed, current acceleration and the predicted operation is included in the carprobe data without considering neural data. The future position may be estimated at various time frames in the future, for example, the future position is calculated at 1 second into the future and the carprobe data may be cached or transmitted every 1 second.

At 212 the link ID from a map is obtained. A rule-based determination may be estimated by an agent (i.e., a real-time virtual cache) by examining the future position of the originating vehicle with the events associated with the link ID. For example, a rule-based determination is made by an agent to examine the future position of the originating vehicle with a static event associated with the link ID.

A static event (i.e., a road event) may include an unsafe event that happens by the action of a single vehicle and may not require communication with a server. For example, the vehicle mounted device may cache the static events and no other car may be in the vicinity for the purposes of communication regarding the event or unsafe condition. A static event may include events such as approaching obstacles or entering a no-entry road. A static event may also include items on the road, such as a traffic signs indicating one-way traffic allowed or a traffic sign indicating that no entry is permitted on a particular road. An IoT device, sensor or camera on mounted on a vehicle may, for example, read and analyze signs on a road. A static structure may include objects on the road, such as construction cones, sidewalks, an animal that is not moving, a pedestrian standing in the road or a parked or stalled vehicle in the road.

The collision mitigation program 110a, 110b may also determine by the link ID if the driving operation is unsafe. An agent on a vehicle mounted device may determine if the vehicle may encounter an unsafe event at a future position. For example, if the calculated future position is closer than a particular distance, then the agent determines that the situation is unsafe, such as driving the wrong direction on a road.

At 214, the future position with a link ID is transmitted to a server 112. The future position with a link ID may be transmitted to the server via a gateway. Whether neural data was detected at 206 or not detected at 206, the future position may be transmitted. If neural data was detected, then a predicted human motion processing time using an EEG headset may, for example, be included in the carprobe data to be transmitted. An operation detector may compile the input data, the carprobe data with or without neural data, the link ID and the calculated future position for transmitting the data to a dynamic event, for example, an event that may communicate with a server and other surrounding vehicles.

For example, the following future position data may be transmitted:

| Future Position Carprobe Data |
|---|
| Longitude = 139.02 |
| Latitude = 35.46 |
| Link ID = 2 |
| Right = True |

At 216, the static event is detected. If a static event is detected, then an alert or a forced operation may be performed. An alert may be announced to the originating vehicle driver, for example, on a smart phone, through the vehicle speakers or from a vehicle mounted device. A forced operation may also be performed, such as breaking or imposing restrictions to the driving operations of a vehicle, based on the determination result of the cached static events. The forced operation application may, for example, be chosen by the user for both the threshold of when to alert the user and the threshold of when and under what conditions to perform a forced operation.

Figure 3:
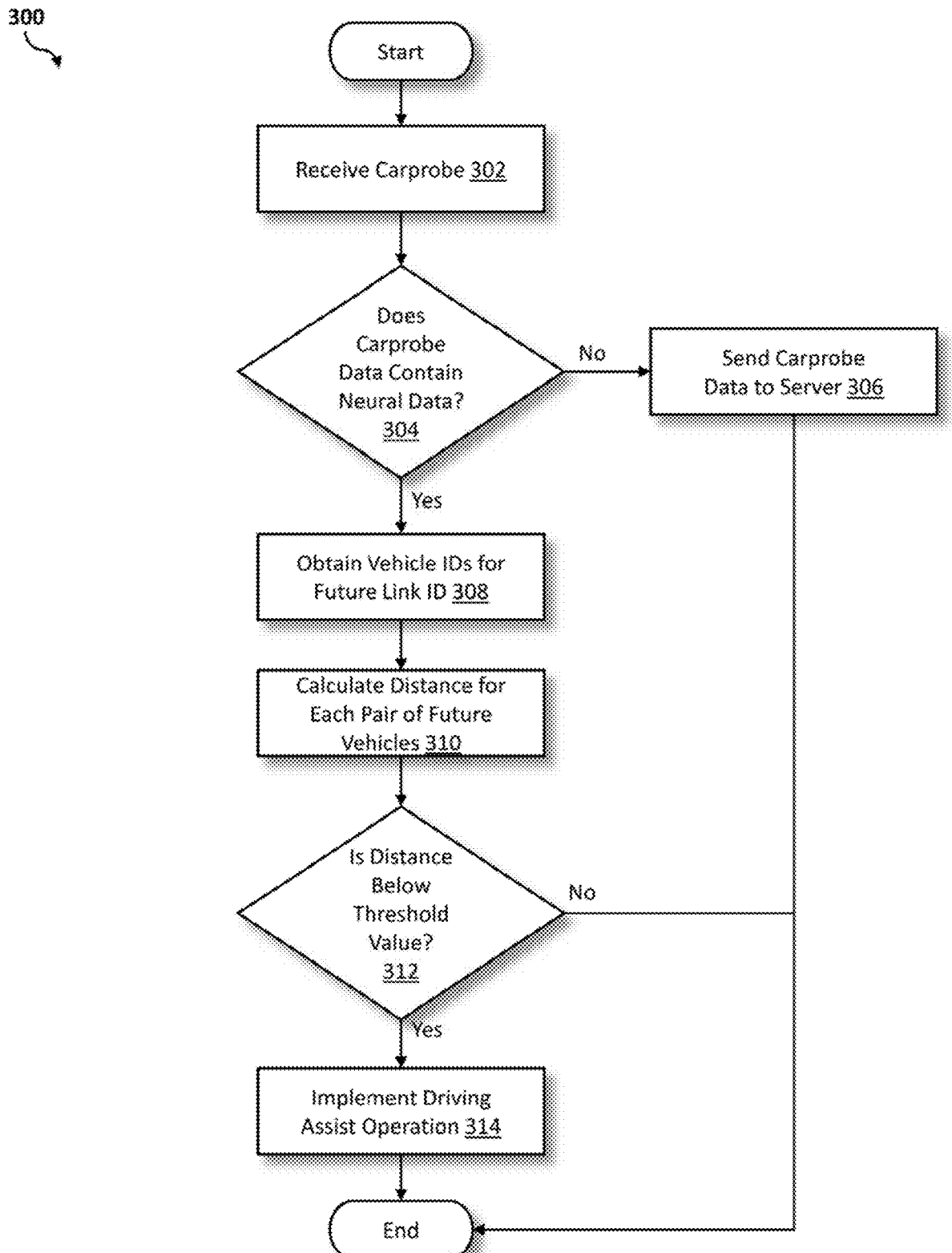
FIG. 3 is an operational flowchart illustrating an event process for a cache update and collision detection on a vehicle-mounted device and a server according to at least one embodiment.

Referring now to FIG. 3, an operational flowchart illustrating the exemplary event for a cache update and collision detection on a vehicle-mounted device and a server process 300 used by the collision mitigation program 110a, 110b according to at least one embodiment is depicted.

At 302, carprobe data is received. The carprobe data may be received by the operation detector that has compiled input data, the carprobe data, the link ID and the calculated future position from step 214.

At 304, the collision mitigation program 110a, 110b determines if the carprobe data contains neural data (i.e., brain activity data). The data received at 302 from the operation detector may or may not have included brain activity data. Brain activity data may be determined to be present if, for example, an EEG measurement was incorporated into the operation detector transmitted carprobe data.

If the collision mitigation program 110a, 110b determines that the carprobe data does not contain neural data at 304, then the carprobe data is sent to the server at 306. The carprobe data may be transmitted to the server 112 via the gateway.

If the collision mitigation program 110a, 110b determines that the carprobe data contains neural data at 304, then the vehicle ID for a future link ID is obtained at 308. If the carprobe data contains brain activity data, then an EEG measurement may be present in the carprobe data and the carprobe data may be transmitted directly to the server agent for a rule-based determination and bypass the operation detector and the gateway. For example, a rule engine may handle multiple carprobes sent from nearby moving vehicles on mobile object servers and may match dynamic events on event servers. The carprobes data and events may be processed on rule analysis components. By sending the future position of the originating vehicle to the rule analysis component, an unsafe situation may be detected.

At 220 the future dynamic position link ID from a map is obtained. A rule-based determination may be estimated by an agent (i.e. a real-time virtual cache) by examining the future position of the originating vehicle with dynamic events associated with the link ID. A dynamic event may include a situation occurring on the road within a relatively short time span, such as an event that has a start time and an end time in some case. Examples of dynamic events may include obstacles on the road, animals on the road or other vehicles on the road. A dynamic event example may also include a vehicle-to-vehicle event such as a collision accident or a rapid approach towards a collision. The dynamic events may involve moving objects or stationary objects.

In addition to the rule-based determination estimated by an agent, the future dynamic event information may also be collected on a server by transmitting the data, for example, from a vehicle mounted device to a server (e.g., server 112) over a communication network 116. Collecting dynamic event information on a server may allow the data to be shared with other vehicles and check if it is expired periodically. After an event is detected, the event may be, for example, checked by other surrounding vehicles to determine if the event has expired (e.g., animal or obstruction on the road moves away from the road).

At 222, the future vehicle IDs (VIDs) for the future dynamic link IDs (i.e., link IDs) are obtained. Obtaining the link ID from a map may include, for example, finding the ID of the road predicted for when the vehicle is in a future position. The future position may be calculated using the brain activity data included in intermediate data. Intermediate data may be used to find the future vehicle position that may collide with a surrounding vehicle. Intermediate data may be, for example, a key-value store. The key may represent the link ID and the value may represent the current or future vehicle ID on the link (i.e., road). The VID may be an ID that is unique for each vehicle.

A future link ID may be the link ID of the vehicle on the road at a future point in time. The future position may be estimated at various time frames in the future, for example, the future position is calculated at 1 second into the future and the carprobe data may be cached or transmitted every 0.1 second. Since each vehicle on the road (i.e., the link) may have a unique VID, intermediate data may be calculated or predicted based on the future position of the originating VID (e.g., VID1) and other vehicles on the link. For example, a link cache for future vehicle positions may occur as follows:

| Intermediate Data | | |
|---|---|---|
| Link ID | Current Vehicle IDs | Future Vehicle IDs |
| 1 | VID1 | |
| 2 | VID2 | VID1, VID2 | where VID1 and VID2 represent Vehicle ID 1 (e.g., the originating vehicle ID) and Vehicle ID 2 associated with the Link ID.

Then, at 310 the distance for each pair of future vehicles are calculated. A calculation may be made between a distance of a future originating vehicle position and a future second vehicle position. A vehicle agent of the originating vehicle may receive carprobe data directly from the gateway handler. The vehicle agent may get the future positions of other vehicles associated with the link ID on the basis of the link ID of the originating vehicle that was included in the received carprobe. The vehicle agent may compare the future position of the originating vehicle with the future position of the other vehicles. For example, if the shortest distance between 2 vehicles is below a predetermined distance, the longitude and latitude obtained from a GPS may be calculated at the future position.

At 312, the collision mitigation program 110a, 110b determines if the calculated distance is below a threshold value. The predetermined distance, for example, may be set to varying distances depending on the type and size of a vehicle. For example, a larger commercial vehicle may require a larger predetermined distance than a small compact car.

If the collision mitigation program 110a, 110b determines that the calculated distance is below a threshold value at 312, then a driving assist operation is implemented at 314. A driving assist operation may include an alert of a forced operation. The threshold distance may include various distances, such as varying distances depending on a vehicle size. The user may also, for example, choose the conditions in which to receive an alert or to allow a forced operation to be performed. For example, an alert may issue a notification to nearby vehicles in 0.1 second using an IoT4A framework. If the originating vehicle determines a risk of a collision or a rapid approach of an incident, then a notification or a forced operation may be performed as a default setting or as set by a user.

If the collision mitigation program 110a, 110b determines that the calculated distance is above a threshold value at 312, then the collision mitigation program ends (i.e., no alert or forced operation).

Figure 4A:
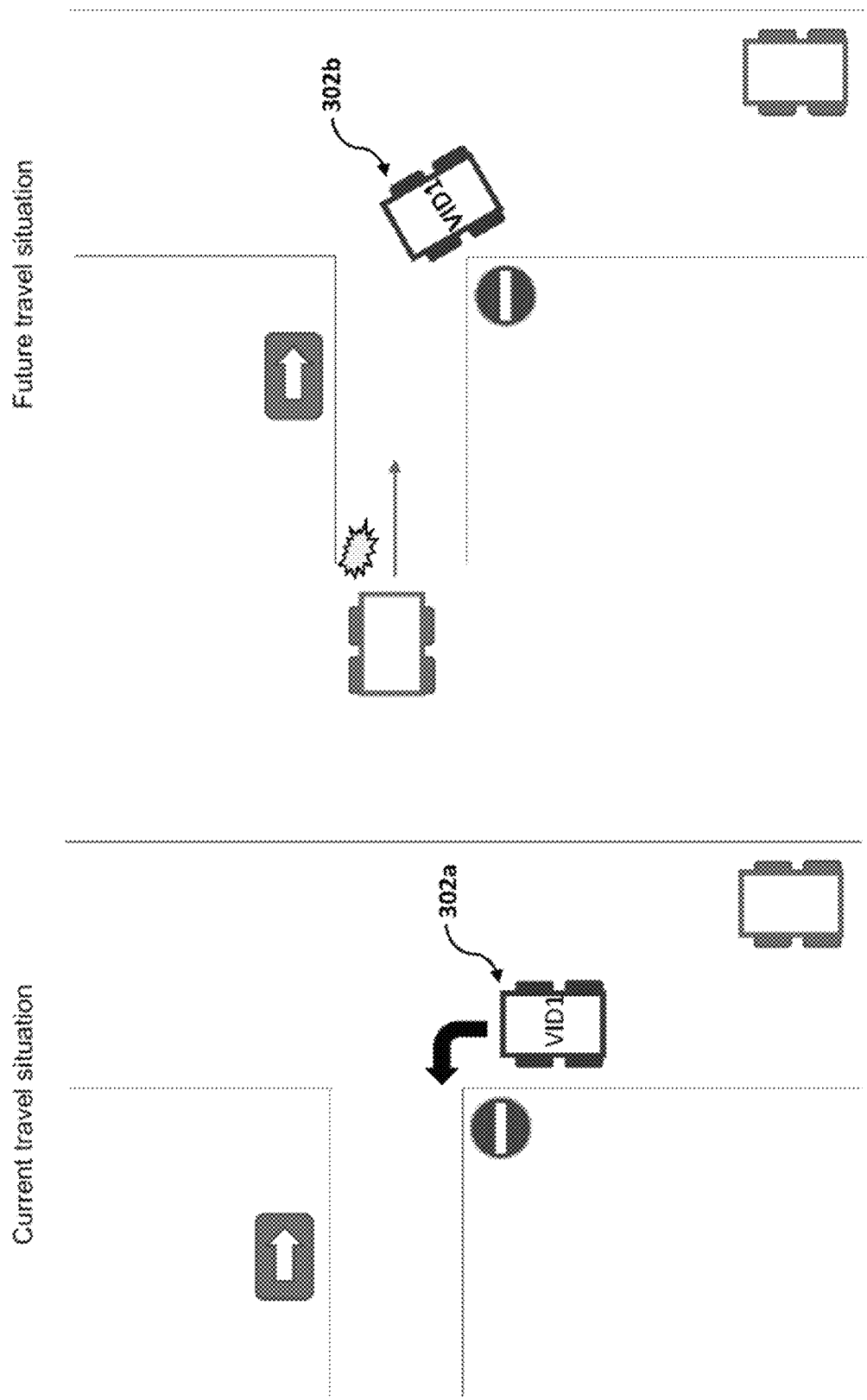
FIG. 4A is a block diagram of a vehicle to map event example according to at least one embodiment.

Referring now to FIG. 4A, a block diagram of a vehicle to map event example used by the collision mitigation program 110a, 110b according to at least one embodiment is depicted. The current travel situation may be determined based on the carprobe data and map data for VID1 302a. Map matching may combine the carprobe and map data to determine the current location and link ID for VID1 302a. The future position may be calculated for VID1 302b with brain activity data and the future position may be estimated at various time frames in the future based on the current traveling direction, current speed, current accelerations and predicted operations of the driver of the originating vehicle. The future position of VID1 302b may be estimated, for example, at 10 seconds into the future. The carprobe data may be cached every 1 second. At each cache, the current location of VID1 302a may be calculated and as VID1 302a veers towards the wrong way down a one-way road, then the future travel situation for VID1 302b may create an alert or a forced stop for the originating driver of VID1 302a, b.

Figure 4B:
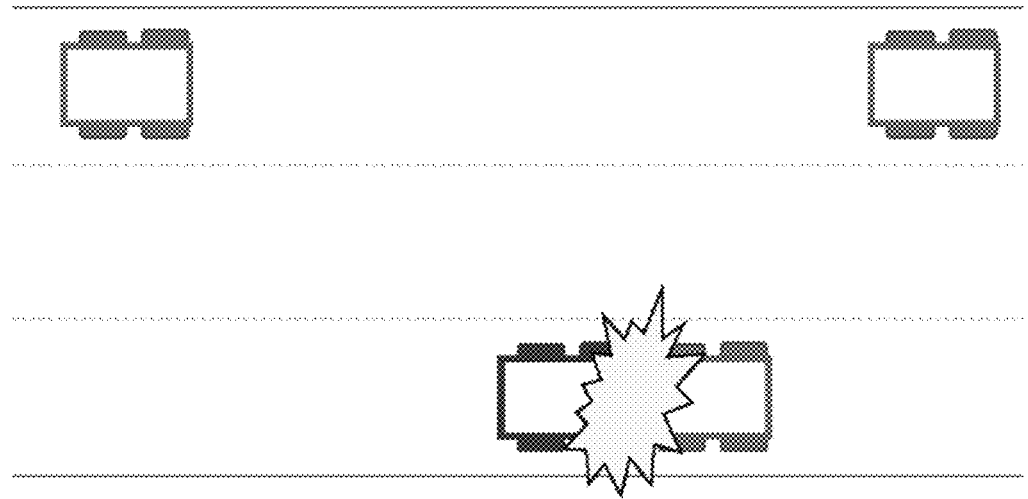
FIG. 4B is a block diagram of a vehicle to vehicle event example according to at least one embodiment.
Figure 4B:
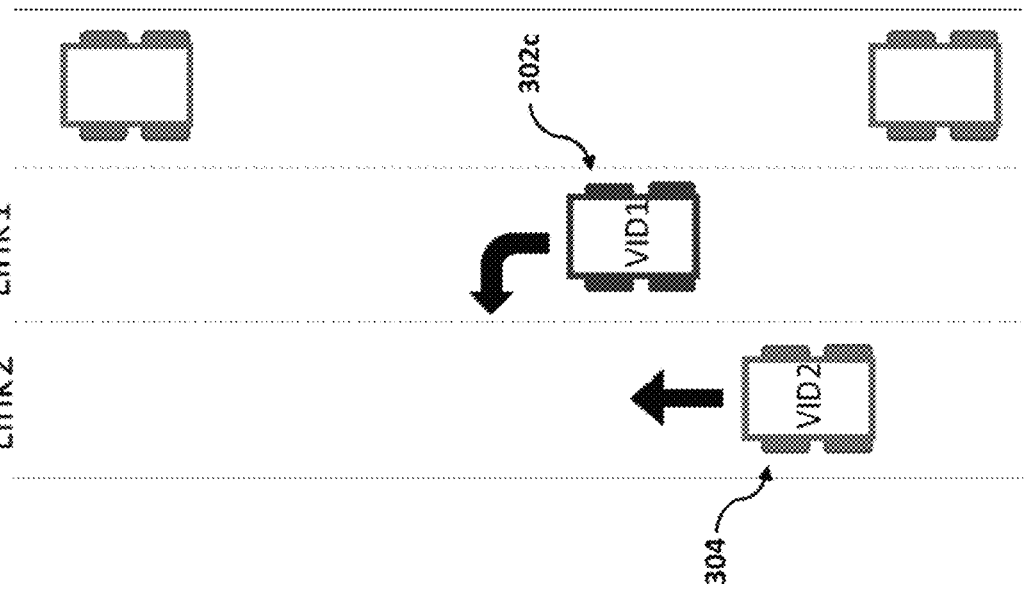

Referring now to FIG. 4B, a block diagram of a vehicle to vehicle event example used by the collision mitigation program 110a, 110b according to at least one embodiment is depicted. The current travel situation for the originating driver VID1 302c may be determined based on map data, brain activity data and carprobe data. Map matching may combine the VID1 302c link ID with the VID1 302c carprobe data, which includes brain activity data. Map matching may include a method to modify raw latitude and longitude data based on map data and then map to a position on the actual road.

The future position may be calculated using EEG measurements for the driver of originating vehicle VID1 302c, the current speed, the current acceleration and the current traveling direction. The future position is predicted, for example, 1 second into the future and the carprobe data may be cached every 0.1 second by obtaining a future dynamic link ID. The link ID may represent a position on the road where the originating vehicle VID1 302c is anticipated to be at. The distance between VID1 302c may be calculated with reference to VID2 304 and if the distance is below a threshold distance, then the collision mitigation program 110a, 110b may alert both vehicles, VID1 302c and VID2 304, or may perform a forced stop of the originating vehicle driver VID1 302c.

It may be appreciated that FIGS. 2, 3, 4A and 4B provide only an illustration of one embodiment and do not imply any limitations with regard to how different embodiments may be implemented. Many modifications to the depicted embodiment(s) may be made based on design and implementation requirements.

Figure 5:
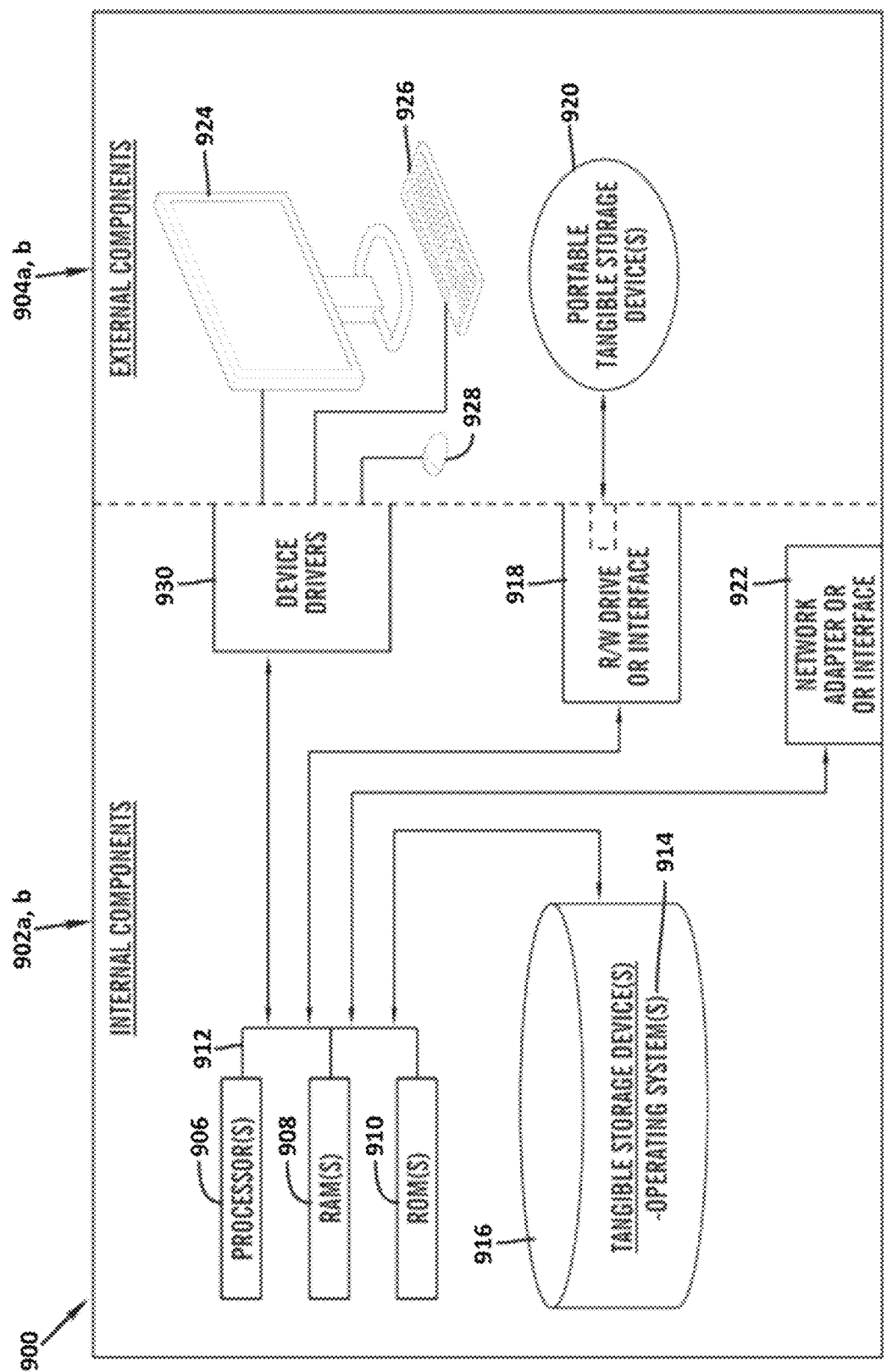
FIG. 5 is a block diagram of internal and external components of computers and servers depicted in FIG. 1 according to at least one embodiment.

FIG. 5 is a block diagram 900 of internal and external components of computers depicted in FIG. 1 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 *a, b* and external components 904 *a, b* illustrated in FIG. 5. Each of the sets of internal components 902 *a, b* includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the collision mitigation program 110a in client computer 102, and the collision mitigation program 110b in network server 112, may be stored on one or more computer-readable tangible storage devices 916 for execution by one or more processors 906 via one or more RAMs 908 (which typically include cache memory). In the embodiment illustrated in FIG. 5, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 *a, b* also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the collision mitigation program 110a, 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The software program 108 and the collision mitigation program 110a in client computer 102 and the collision mitigation program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the collision mitigation program 110a in client computer 102 and the collision mitigation program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, EEG machines, BCI machines and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
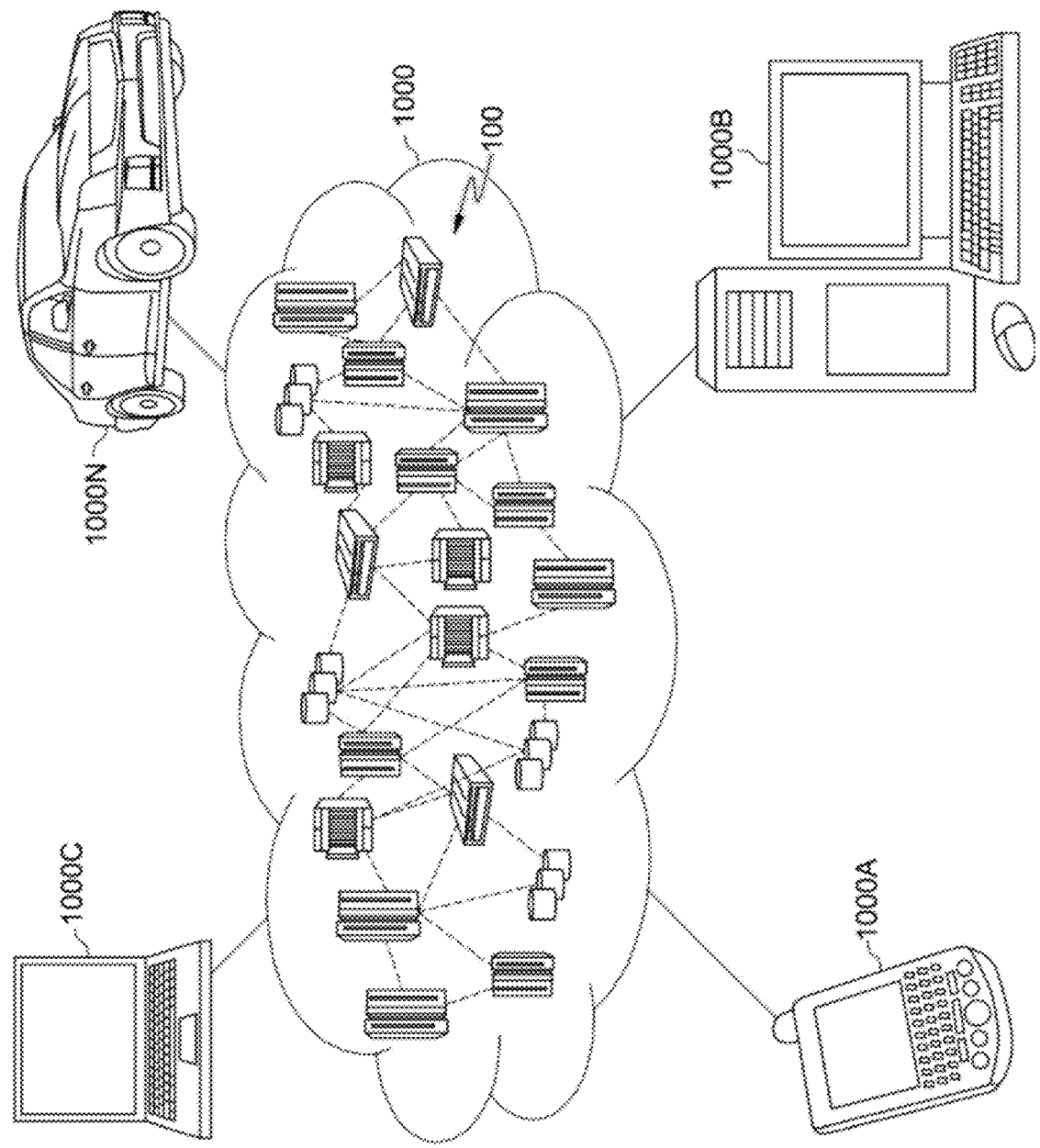
FIG. 6 is a block diagram of an illustrative cloud computing environment including the computer system depicted in FIG. 1, in accordance with an embodiment of the present disclosure.

Referring now to FIG. 6, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 6 are intended to be illustrative only and that computing nodes 100 and cloud computing environment 1000 can communicate with any type of computerized device over any type of network and/or network addressable connection (e.g., using a web browser).

Referring now to FIG. 7, a set of functional abstraction layers 1100 provided by cloud computing environment 1000 is shown. It should be understood in advance that the components, layers, and functions shown in FIG. 7 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and collision mitigation 1156. A collision mitigation program 110a, 110b provides a way to predict human motions prior to the fulfillment of the human motion.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for preemptive collision mitigation, the method comprising:
    matching raw global positioning system location coordinates of a first vehicle to coordinates of a mapped road network;
    adding current neural data of an operator of the first vehicle to carprobe data of the first vehicle in response to a difference between the current neural data and stored neural data of the operator exceeding a threshold amount, wherein neural data comprises electroencephalogram (EEG) activity of the operator while performing vehicle operations;
    calculating a future position of the first vehicle based on the carprobe data from the first vehicle comprising a current traveling direction, a current speed, a current acceleration, and a predicted voluntary movement of the operator of the first vehicle, wherein the predicted voluntary movement is determined by the neural data of the operator comprising movement-related cortical potentials;
    caching the carprobe data every one second and estimating the future position at one second intervals into future;
    calculating a distance between the future position of the first vehicle and a future position of a second vehicle; and
    in response to determining the calculated distance between the future position of the first vehicle and the future position of the second vehicle is below a threshold distance, implementing a driving assist operation, wherein the threshold distance varies based on a size of the first vehicle, and wherein the driving assist operation performs a forced breaking operation of the first vehicle.

2. The method of claim 1, wherein the carprobe data collects real-time data relating to traveling locations and timing from Internet-of-Things devices, geographic locations, health status, driver data and events of interest.

3. The method of claim 1, wherein the carprobe data contains a link ID, wherein the link ID includes a unique ID assigned to the road.

4. The method of claim 1, wherein the neural data is collected by an EEG device, wherein the EEG device detects brain activity comprising movement-related cortical potentials which preemptively predicts human motion.

5. The method of claim 1, wherein the driving assist operation creates an alert to the operator of the first vehicle.

6. The method of claim 1, wherein the driving assist operation creates a forced vehicle operation that imposes restrictions to the driving operations of the first vehicle.

7. The method of claim 1, wherein the carprobe data is received on a vehicle-mounted device and a server.

8. A computer system for preemptive collision mitigation, comprising:
one or more processors, one or more computer-readable memories, one or more computer-readable tangible storage media, and program instructions stored on at least one of the one or more computer-readable tangible storage media for execution by at least one of the one or more processors via at least one of the one or more computer-readable memories, wherein the computer system is capable of performing a method comprising:
matching raw global positioning system location coordinates of a first vehicle to coordinates of a mapped road network;
adding current neural data of an operator of the first vehicle to carprobe data of the first vehicle in response to a difference between the current neural data and stored neural data of the operator exceeding a threshold amount, wherein neural data comprises electroencephalogram (EEG) activity of the operator while performing vehicle operations;
calculating a future position of the first vehicle based on the carprobe data from the first vehicle comprising a current traveling direction, a current speed, a current acceleration, and a predicted voluntary movement of the operator of the first vehicle, wherein the predicted voluntary movement is determined by the neural data of the operator comprising movement-related cortical potentials;
caching the carprobe data every one second and estimating the future position at one second intervals into future;
calculating a distance between the future position of the first vehicle and a future position of a second vehicle; and
in response to determining the calculated distance between the future position of the first vehicle and the future position of the second vehicle is below a threshold distance, implementing a driving assist operation, wherein the threshold distance varies based on a size of the first vehicle, and wherein the driving assist operation performs a forced breaking operation of the first vehicle.

9. The computer system of claim 8, wherein the carprobe data collects real-time data relating to traveling locations and timing from Internet-of-Things devices, geographic locations, health status, driver data and events of interest.

10. The computer system of claim 8, wherein the carprobe data contains a link ID, wherein the link ID includes a unique ID assigned to the road.

11. The computer system of claim 8, wherein the neural data is collected by an EEG device, wherein the EEG device detects brain activity comprising movement-related cortical potentials which preemptively predicts human motion.

12. The computer system of claim 8, wherein the driving assist operation creates an alert to the operator of the first vehicle.

13. The computer system of claim 8, wherein the driving assist operation creates a forced vehicle operation that imposes restrictions to the driving operations of the first vehicle.

14. The computer system of claim 8, wherein the carprobe data is received on a vehicle-mounted device and a server.

15. A computer program product for preemptive collision mitigation, comprising:
one or more computer-readable tangible storage media and program instructions stored on at least one of the one or more computer-readable tangible storage media, the program instructions executable by a processor to cause the processor to perform a method comprising:
matching raw global positioning system location coordinates of a first vehicle to coordinates of a mapped road network;
adding current neural data of an operator of the first vehicle to carprobe data of the first vehicle in response to a difference between the current neural data and stored neural data of the operator exceeding a threshold amount, wherein neural data comprises electroencephalogram (EEG) activity of the operator while performing vehicle operations;
calculating a future position of the first vehicle based on the carprobe data from the first vehicle comprising a current traveling direction, a current speed, a current acceleration, and a predicted voluntary movement of the operator of the first vehicle, wherein the predicted voluntary movement is determined by the neural data of the operator comprising movement-related cortical potentials;
caching the carprobe data every one second and estimating the future position at one second intervals into future;
calculating a distance between the future position of the first vehicle and a future position of a second vehicle; and
in response to determining the calculated distance between the future position of the first vehicle and the future position of the second vehicle is below a threshold distance, implementing a driving assist operation, wherein the threshold distance varies based on a size of the first vehicle, and wherein the driving assist operation performs a forced breaking operation of the first vehicle.

16. The computer program product of claim 15, wherein the carprobe data collects real-time data relating to traveling locations and timing from Internet-of-Things devices, geographic locations, health status, driver data and events of interest.

17. The computer program product of claim 15, wherein the carprobe data contains a link ID, wherein the link ID includes a unique ID assigned to the road.

18. The computer program product of claim 15, wherein the neural data is collected by an EEG device, wherein the EEG device detects brain activity comprising movement-related cortical potentials which preemptively predicts human motion.

19. The computer program product of claim 15, wherein the driving assist operation creates an alert to the operator of the first vehicle.

20. The computer program product of claim 15, wherein the driving assist operation creates a forced vehicle operation that imposes restrictions to the driving operations of the first vehicle.

21. The computer program product of claim 15, wherein the carprobe data is received on a vehicle-mounted device and a server.

22. A method for preemptive collision mitigation, the method comprising:

matching raw global positioning system location coordinates of a first vehicle to coordinates of a mapped road network;

adding current neural data of an operator of the first vehicle to carprobe data of the first vehicle in response to a difference between the current neural data and stored neural data of the operator exceeding a threshold amount, wherein neural data comprises electroencephalogram (EEG) activity of the operator while performing vehicle operations;

calculating a future position of the first vehicle based on the carprobe data from the first vehicle comprising a current traveling direction, a current speed, a current acceleration, and a predicted voluntary movement of the operator of the first vehicle, wherein the predicted voluntary movement is determined by the neural data of the operator comprising movement-related cortical potentials;

caching the carprobe data every one second and estimating the future position at one second intervals into future;

determining the calculated future position of the first vehicle will be in a position on a roadway that creates an unsafe driving condition, wherein the calculated future position is below a particular distance, and wherein the particular distance varies based on a size of the first vehicle; and implementing a driving assist operation, wherein the driving assist operation performs a forced breaking operation of the first vehicle.

23. The method of claim 22, wherein the unsafe driving condition is a driving maneuver on the road made by the first vehicle that creates an interaction with a static structure, wherein the static structure is an object on the road.

24. The method of claim 22, wherein the unsafe driving condition on the road is the first vehicle traveling in a wrong-direction on a road.

\* \* \* \* \*